US012472344B2

(12) United States Patent
Cabane et al.

(10) Patent No.: US 12,472,344 B2

(45) Date of Patent: Nov. 18, 2025

(54) LEFT VENTRICLE UNLOADING DEVICE

(71) Applicant: SYSTOL DYNAMICS, Marseilles (FR)

(72) Inventors: Vincent Cabane, Paris (FR); Alain Cornen, Marseilles (FR)

(73) Assignee: SYSTOL DYNAMICS, Marseilles (FR)

(*) Notice: Subject to any disclaimer, the term of this patent is extended or adjusted under 35 U.S.C. 154(b) by 410 days.

(21) Appl. No.: 17/927,835

(22) PCT Filed: May 26, 2021

(86) PCT No.: PCT/EP2021/064059
§ 371 (c)(1),
(2) Date: Nov. 25, 2022

(87) PCT Pub. No.: WO2021/239814
PCT Pub. Date: Dec. 2, 2021

(65) Prior Publication Data

US 2023/0211143 A1 Jul. 6, 2023

(30) Foreign Application Priority Data

May 26, 2020 (EP) .................................... 20305549

(51) Int. Cl.
*A61M 60/139* (2021.01)
*A61M 60/148* (2021.01)
*A61M 60/569* (2021.01)

(52) U.S. Cl.
CPC ........ *A61M 60/139* (2021.01); *A61M 60/148* (2021.01); *A61M 60/569* (2021.01)

(58) Field of Classification Search
CPC ........ A61F 2/82; A61F 2002/068; A61F 2/07; A61F 2/90; A61F 2/95; A61F 2210/009; A61F 2230/001; A61M 60/139; A61M 60/148; A61M 60/216; A61M 60/237; A61M 60/419; A61M 60/422;
(Continued)

(56) References Cited

U.S. PATENT DOCUMENTS

| | | | |
|---|---|---|---|
| 5,290,227 A | 3/1994 | Pasque et al. |
| 2015/0231318 A1 | 8/2015 | Bulent et al. |

(Continued)

OTHER PUBLICATIONS

International Search Report issued on Oct. 13, 2021, in corresponding International Application No. PCT/EP2021/064059, 6 pages.

*Primary Examiner* — Jon Eric C Morales
(74) *Attorney, Agent, or Firm* — Maier & Maier, PLLC

(57) ABSTRACT

A ventricle unloading device intended to be implanted inside a patient's blood vessel portion through which a blood flow circulates. The device includes: a stator, a rotor arranged around the stator, the rotor having a driving impeller and a impeller engine, the impeller being an unducted impeller aimed at rotating freely within the blood vessel portion, and a static anchoring element displaying a circular part which is configured to extend around the impeller. The circular part of the static anchoring element defines a circulation area intended to contain the entire blood flow circulating through the blood vessel portion, the activation of the rotor is a pulsatile activation, and the activation is synchronized with the patient's heart contraction.

14 Claims, 5 Drawing Sheets

(58) Field of Classification Search
CPC ................ A61M 60/82; A61M 60/824; A61M 2205/0238; A61M 2205/0266; A61M 2205/3365; A61M 2205/3507; A61M 2210/127; A61M 2230/04; A61M 60/13; A61M 60/178; A61M 60/221; A61M 60/31; A61M 60/33; A61M 60/408; A61M 60/414; A61M 60/515; A61M 60/538; A61M 60/562; A61M 60/569; A61M 60/585; A61M 60/804; A61M 60/806; A61M 60/808; A61M 60/81; A61M 60/812; A61M 60/833; A61M 60/857; A61M 60/861; A61M 60/873; A61M 60/88
See application file for complete search history.

(56) References Cited

U.S. PATENT DOCUMENTS

| | | | | |
|---|---|---|---|---|
| 2015/0367050 | A1 | 12/2015 | Bulent et al. | |
| 2019/0351120 | A1* | 11/2019 | Kushwaha .......... | A61M 60/237 |
| 2020/0405926 | A1* | 12/2020 | Alexander .......... | A61M 60/148 |

* cited by examiner

LEFT VENTRICLE UNLOADING DEVICE

FIELD

The invention generally relates to mechanical circulatory support and methods.

BACKGROUND

It is known that the human heart includes a right ventricle, which is used for circulation of venous blood (blue blood) and a left ventricle which serves for the circulation of arterial blood (red blood).

The blood from the venous system arrives into the right atrium then goes to the right ventricle through the tricuspid valve and leaves therefrom through the pulmonary artery which transports blood to the lungs. Coming out of the lungs, oxygenated blood returns to the heart through the pulmonary veins, arrives into the left atrium then goes to the left ventricle through the mitral valve and leaves therefrom through the aorta towards the arterial system. The aorta is the main artery that carries oxygen-rich blood from your heart to the body.

In the vast majority of cases, heart diseases originate in the left ventricle.

As well known by any person skilled in the art, a ventricular assist device (VAD) is a mechanical pump that's used to support heart function and blood flow for patients who have weakened hearts. Usually, the device takes blood from a lower chamber of the heart and helps to pump it to the body and vital organs, just as a healthy heart would.

A VAD may be used if one of the heart's lower chamber (the right or the left ventricle) doesn't work properly; in case of dysfunction of the two ventricles two VADs or a total artificial heart are needed.

In the state of the art, a VAD can help a patient if their ventricles don't work well due to heart disease. A VAD can for example help support a heart:

- during or after surgery, until the heart recovers,
- while a patient is waiting for a heart transplant,
- if a person is not eligible for a heart transplant, a VAD may be a long-term solution to support heart function and blood flow.

Knowingly, the basic parts of a VAD include: a small tube that carries blood out of the patient's heart into a pump; another tube that carries blood from the pump to the blood vessels. Some VADs pump blood like the heart does, with a pumping action. Other VADs keep up a continuous flow of blood. The power source is classically connected to a control unit that monitors the VAD's functions.

Knowingly, the basic elements of a VAD include: a tube that carries blood drawn upstream of the patient's heart to a pump; another tube that carries blood from the pump to blood vessels downstream of the heart. They thus perform a bypass. On the other hand, certain VADs pump blood by imitating the heart by carrying out a displacement of volume at regular intervals (pulsatile mode). Conversely, other VADs work like a conventional fluid pump and propel a continuous flow of blood (continuous mode).

The two basic types of VADs are a left ventricular assist device and a right ventricular assist device. The left ventricular assist device is the most common type of VAD. It helps the left ventricle pump blood to the aorta.

Right ventricular assist devices are usually used alone only for short-term support of the right ventricle after left ventricular assist device surgery or another heart surgery. A right ventricular assist device helps the right ventricle pump blood to the pulmonary artery.

It is well known to use a pump to assist the heart in circulating blood in replacement of the left ventricle. This pump is typically part of a bypass arrangement implanted in parallel with the left ventricle. Such a bypass system includes, in addition to the pump, an upstream end connected to a left ventricular tip and the other end connected to the inlet opening of the pump, and a downstream conduit having an extremity connected to a discharge opening of the pump and the other end connected to the aorta at the outlet of the left ventricle.

However, if the heart is bypassed, it may lose its ability to recover, due to the increase of the left ventricle post load.

Further solutions suggest serial implantations and does not necessarily bypass the heart. Document WO2013148697, for example, discloses a cardiac pump which aims at adjusting the pressure of the blood flow in a human body including one or more flow modification elements, where said flow modification elements direct the blood flow to a desired organ or a desired vessel. The position or orientation of the pumps and flow modification elements may be oriented to assist native blood flow, increase or decrease pressure in a region, direct the blood flow in a direction opposite of native flow, direct flow towards desired vessel(s) or organ(s), or a combination thereof. Another example for such a cardiac assist device is to be found in document U.S. Pat. No. 10,420,869 B2 which discloses a cardiac assist device implanted in the ascending aorta, more precisely implanted in the location of a section of the aorta that has been removed.

However, those devices do no synchronize with the natural heart rhythm of the patient and do therefore not allow an effective, fast and safe physiological recovery of the patient's heart.

The objective of the present invention is to treat cardiac insufficiency by enabling physiological recovery of the heart. This is best achieved by unloading the left ventricle while preserving the cardiac architecture.

SUMMARY

This objective is reached by means of the present invention relating to a ventricle unloading device intended to be serially implanted inside a patient's blood vessel portion through which a blood flow circulates, said device comprising:

- a stator,
- a rotor arranged around the stator, the rotor comprising a blood driving impeller and at least a part of an impeller engine, the impeller comprising a hub and at least one blade displaying an attachment area to the hub, the impeller further being an unducted impeller aimed at rotating freely within the blood vessel portion,
- a static anchoring element displaying a circular part which is configured to extend around the impeller, wherein the circular part of the static anchoring element defines a circulation area intended to contain the entire blood flow circulating through the blood vessel portion, wherein the activation of the rotor is a pulsatile activation and that said activation is synchronized with the patient's heart contraction.

Mechanically circulating the entire blood flow enables to optimise performance regarding flow mechanics, to optimally reduce haemolysis and, last but not least, to maximise the workload taken off the heart, as the heart does not need to spend power in order to circulate said blood flow.

The device according to the present invention may also include one or several of the following features, taken separately or in combination which each other:

- the circular part of the static anchoring element is configured to extend against a wall of the blood vessel portion and to cooperate by friction with said wall,
- the circular part of the static anchoring element is configured to form at least a part of a wall of the blood vessel portion,
- the circular part of the static anchoring element comprises a rigid body and two soft and flexible extremities in order to enable anastomosis,
- the device is located in the patient's ascending aorta,
- the impeller is made of a foldable material,
- the impeller engine is located inside the impeller hub,
- the impeller displays a length comprised between 20 and 50 mm,
- the pulsatile activation of the impeller engine comprises two phases:
  - a mechanical phase during which the impeller is rotated by the patient's natural blood flow,
  - an electrical phase during which the impeller is rotated by the impeller engine,
- the mechanical phase of the activation generates an electric current, said electric current inducing the electrical phase of the activation,
- the pulsatile activation of the impeller is induced by signals sensed by electrical sensors,
- the rotation direction of the impeller depends on the natural direction of the patient's blood flow rotation,
- the device comprises a second impeller, said second impeller extending along the stator and being driven by a second impeller engine, the rotation direction of the second impeller being opposite to the rotation direction of the impeller
- the device comprises a second impeller, said second impeller extending along the stator, both impeller being driven by the impeller engine, the second impeller being connected to the impeller engine by means of an epicyclic gear train in order to allow the second impeller rotation direction to be opposite to the rotation direction of the impeller.

DETAILED DESCRIPTION

The following detailed description will be better understood when read in conjunction with the drawings. For the purpose of illustrating, the device is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

Figure 1A:
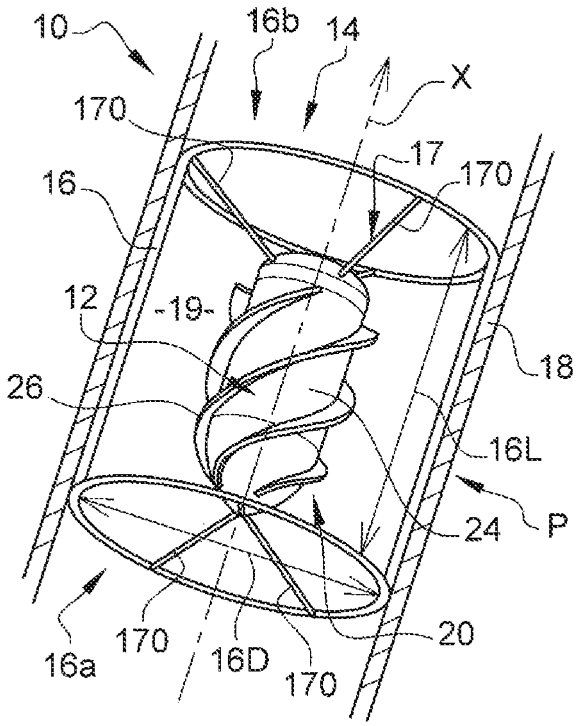
FIG. 1A is a general schematic view of the invention.
Figure 1B:
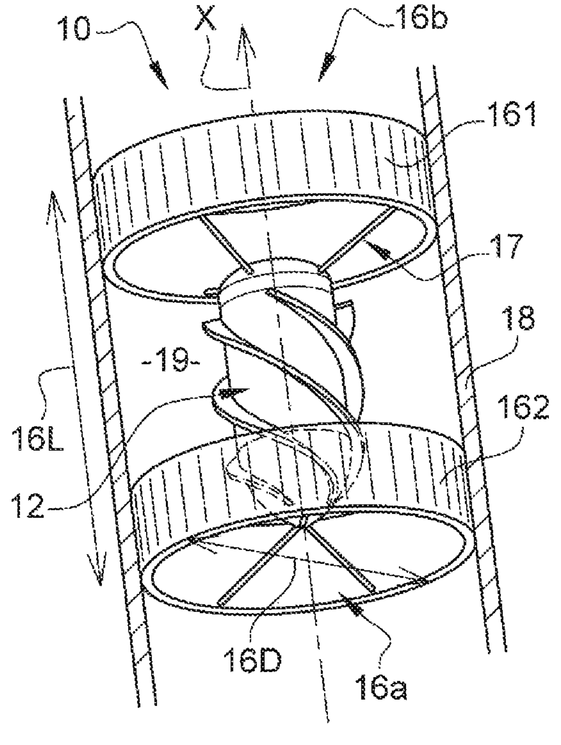
FIG. 1B is a general schematic view of the invention according to an alternative embodiment.
Figure 2A:
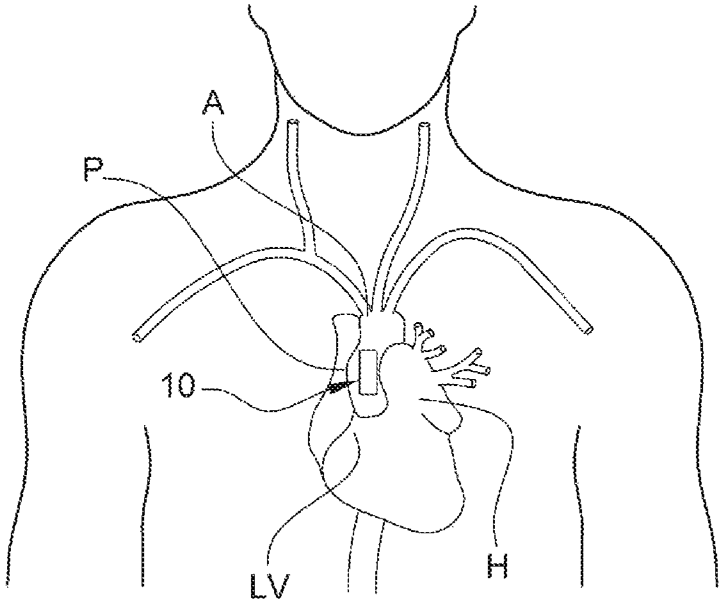
FIG. 2A is a schematic view of the device implanted inside a patient.

As can be seen on FIGS. 1A, 1B and 2A, the ventricle unloading device 10 according to the present invention, is intended to be implanted inside a patient's blood vessel portion P through which a blood flow circulates. The blood vessel defines an axial direction X along which the blood flow circulates.

More precisely, on FIG. 2A it is to be seen that the unloading device 10 is configured to be serially implanted inside a blood vessel portion P situated inside the ascending aorta A.

Figure 2B:
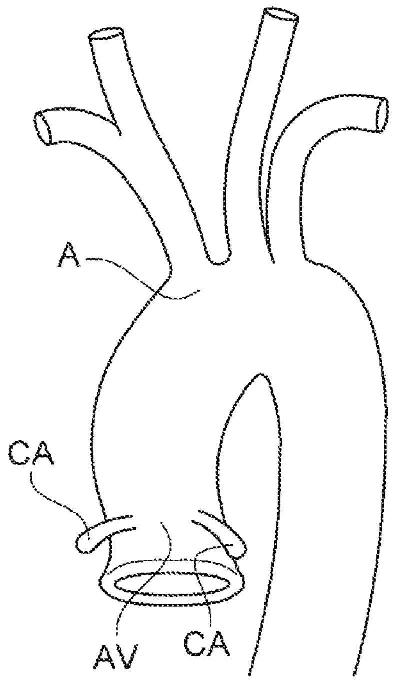
FIG. 2B is a schematic view of the ascending aorta of a patient.

The wording "serially implanted" refers to a configuration in which the device 10 is implanted in the native circulatory system of a patient. More precisely, in the current case, the device 10 is implanted at the exit of the heart H and that the blood flow crosses the heart H before entering the device 10. Alternatively, "parallelly implanted" refers to a device that leads the blood flow to bypass whole or part of the heart H. The ascending aorta A is a portion of the aorta commencing at the upper part of the base of the left ventricle LV of the heart H. The ascending aorta starts just after the coronary arteries until the brachio-cephalic artery. The ascending aorta A passes obliquely upward (in direction of the patient's head), forward (in direction of the patient's chest), and to the right (in direction of the patient's right side), as can be grasped from FIG. 2B. The total length of the ascending aorta A is about 3 to 6 cm and its diameter is around 30 mm. As known to a person of skill in the art, the diameter of the aorta can vary depending on the age and sex of the patient.

As already mentioned, the objective of the present invention is to treat cardiac insufficiency by enabling physiological recovery of the heart H. This is achieved by unloading the left ventricle LV while preserving the cardiac architecture in order to allow a recovery of said left ventricle LV. As the left ventricle LV of the weakened heart H cannot push the blood hard enough to unload itself anymore, the left ventricle unloading function has to be assisted. However, in order to rehabilitate the left ventricle LV, it also has to be preserved and re-trained into health, like any other muscle. The device 10 therefore displays a size and shape that allows the least invasive possible implantation and removal.

As can be seen on FIGS. 1A and 1B, the device 10 comprises three parts:

- a stator X',
- a rotor 12,
- and a static anchoring element 14.

The stator X' forms a static rotation axis of the rotor 12 and extends along the axial direction X.

The static anchoring element 14 displays itself two parts:

- a circular part 16 extending around the rotor 12,
- a connection structure 17 connecting the stator X' to the circular part 16.

In a first embodiment, not shown, the circular part 16 of the static anchoring element 14 is configured to form at least a part of a wall 18 of the blood vessel portion P. In this case, the natural biological wall 18 of the blood vessel portion P is partly or completely replaced by the circular part 16 and the device 10 is surgically implanted in the blood vessel portion P, using a sternotomy or preferably a thoracotomy approach.

In the illustrated embodiments, the circular part 16 bears against a wall 18 of the blood vessel portion P. The natural biological wall 18 of the blood vessel portion P is conserved. More precisely, the circular part 16 of the static anchoring element 14 is aimed at being in contact and to cooperate by friction with the wall 18 of the blood vessel portion P.

As well known in physics, friction is the force resisting the relative motion of solid surfaces, fluid layers, and material elements sliding against each other. Therefore, two elements cooperating by friction are not sliding against each other and remain motionless relatively to each other.

This way, once the device 10 is implanted inside the patient, no blood (or almost no blood) is circulating between the circular part 16 of the static anchoring element 14 and the wall 18 of the blood vessel portion P. The close contact between the circular part 16 also enables a harmonious weight distributing of the device 10 over the wall 18 and thus to avoid any high pressure point that could lead to damaging the blood vessel portion P. In this case, the circular part 16 allows an atraumatic anchoring of the device 10 inside a patient: the device 10 is introduced in the blood vessel portion P either surgically or with a transcatheter approach.

In some embodiments, the circular part 16 may be disconnected from the rotor 12 in order to ease the implantation.

In the embodiment illustrated on FIG. 1A, the circular part 16 of the static anchoring element 14 forms a ferrule. It is made of one single part. The ferrule has an upstream and a downstream (with regards to the blood flow direction X) apertures 16*a*, 16*b*. The upstream aperture 16*a* forms an inlet opening and the downstream aperture 16*b* forms a discharge opening. While the device 10 is in operation, the blood flow enters the ferrule through the upstream aperture 16*a* forming inlet opening and leaves the ferrule through the downstream aperture 16*b* forming discharge opening. The inlet opening 16*a* and discharge opening 1*b* are aligned along the axial direction X. The inlet opening 16*a* and discharge opening 16*b* of the ferrule have the same, or similar, diameter 16D. This diameter 16D is comprised between 15 and 45 mm, preferably 30 mm. Once implanted inside the blood vessel portion P, this ferrule extends along the axial direction X along which the blood flow circulates and contains the entire blood flow circulating through the blood vessel portion P. This means that the whole blood flow entering the patient's aorta passes through the circular part 6 of the static anchoring element 14. In the embodiment shown on FIG. 1A, the circular part 16 of the static anchoring element 14 is a vascular endoprosthesis. In case the wall 18 of the blood vessel portion P is replaced by the circular part 16, said circular par 16 is a vascular prosthesis. In this embodiment, the circular part 16 comprises a rigid body and two soft and flexible extremities, said extremities enabling to secure it to the blood vessel. This securing is technically known as surgical anastomosis. It is generally known, that an anastomosis is a connection or opening between two cavities or passages that are normally diverging or branching, such as between blood vessels, leaf veins, or streams. Such a connection may be natural or artificial and is then called surgical anastomosis.

As already mentioned, mechanically circulating the entire blood flow enables to optimise performance regarding flow mechanics, to optimally reduce haemolysis and, last but not least, to maximise the workload taken off the heart, as the heart does not need to spend power in order to circulate said blood flow. The heart is thus less solicited and less likely to be more damaged.

In the alternative embodiment illustrated on FIG. 1B, the circular part 16 comprises two separated parts 161, 162. The upstream part 161 forms the inlet opening 16*a*, and the downstream part 161 forms the discharge opening 16*b*. Both parts display a general circle shape and abut, both, against the natural wall 18 of the blood vessel portion P. They both, together, define the circulation area 19. This embodiment allows to lighten the device 10.

To allow implantation of the device 10 inside a patient, the length of the device 10 to be implanted has to be shorter than the length of the blood vessel portion P. The device length (and therefore the circular part 16 length 16L) should therefore be comprised between 80 to 100% of the blood vessel portion P length. This would lead to an average length comprised between 40 and 50 mm. Said blood vessel portion P has an average diameter of 30 mm, generally between 25 and 45 mm. The circular part 16 could typically be made of or comprise shape-memory alloy, potentially covered with synthetic materials such as PTFE. It could also or further be made of or comprise some nitinol (a 50-50% Ni—Ti alloy). The circular part 16 has a diameter comprised between 15 mm and 45 mm, and a length comprised between 25 mm and 75 mm.

The circular part 16 of the static anchoring element 14 is anchored inside the blood vessel portion P, by means of the frictional force resulting from the circular part 16 bearing against the wall 18 of the blood vessel. The stator X' is connected to the circular part 16 by means of a connection structure 17. This connection structure can be, for example and as illustrated on FIGS. 1A and 1B, a set of struts 170 extending radially from the stator X' extremities; In the embodiment of FIGS. 1A and 1B, three struts 170 extend from each extremity of the stator X' towards the circular part 16 of the static anchoring element 14. The struts 170 display a length of approximately 15 mm. They most likely are made of or comprise shape-memory alloy conferring some flexibility and enabling the device to follow the natural movement of the blood vessel portion P. However, in order to ensure a perfect immobility of the stator X' with regards to the blood vessel portion P, the struts 170 might also be rigid.

The large cross-sectional passage between the circular part 16 of the static anchoring element 14 and the rotor 12 provides good blood circulation through a large available circulation area 19. The diameter of this circulation area 19 is sensibly equal to the diameter of the blood vessel portion P.

As can be seen on FIGS. 1A, 1B, 3A, 3B and 5A, the rotor 12 of the device 10 comprises a blood driving impeller 20 and an impeller engine 22, or a part of an impeller engine 22. The impeller 20 comprises a hub 24 and at least one blade 26 displaying an attachment area 28 to the hub 24. The impeller hub 24 extends along the axial direction X and displays an upstream extremity 24A and a downstream extremity 24B. The impeller hub 24 extends around the stator X' and the impeller 20 rotates around said stator X'. The stator X' is axially blocked by abutting, respectively upwards and downwards against inner surfaces of the upstream extremity 24A and a downstream extremity 24B. The impeller 20 is further an unducted impeller. This leads the impeller 20, once implanted inside the blood vessel portion P, to rotate freely within the blood flow of the vessel portion P. The impeller 20 is maintained and centred within the blood flow by means of the connection structure 17.

The impeller 20 may be made of a shaped memory alloy chosen from NiTinol, Copper-Zinc-Aluminum, Copper-Aluminum-Nickle, Iron-Manganese-Silicon or Copper-Aluminium-Manganese, preferably in NiTinol. In another embodiment, the impeller 20 may be rigid and be made of or comprise some metallic or polymeric material.

The impeller hub 24 displays a length 24L comprised between 20 and 50 mm, preferably comprised between 35 to 45 mm.

Figure 3A:
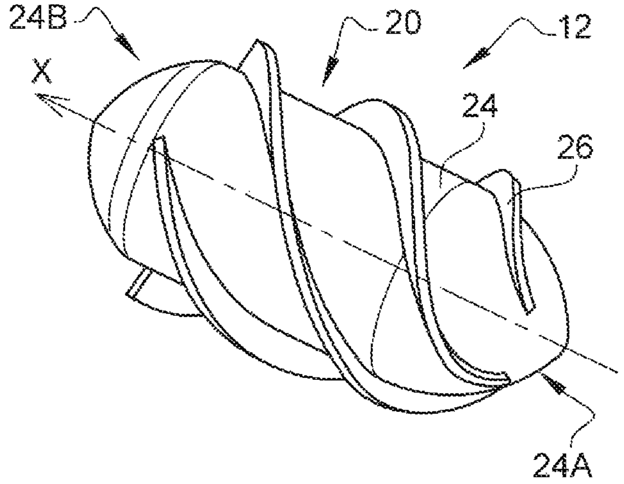
FIG. 3A is a perspective view of a first embodiment of the impeller according to the invention.
Figure 4A:
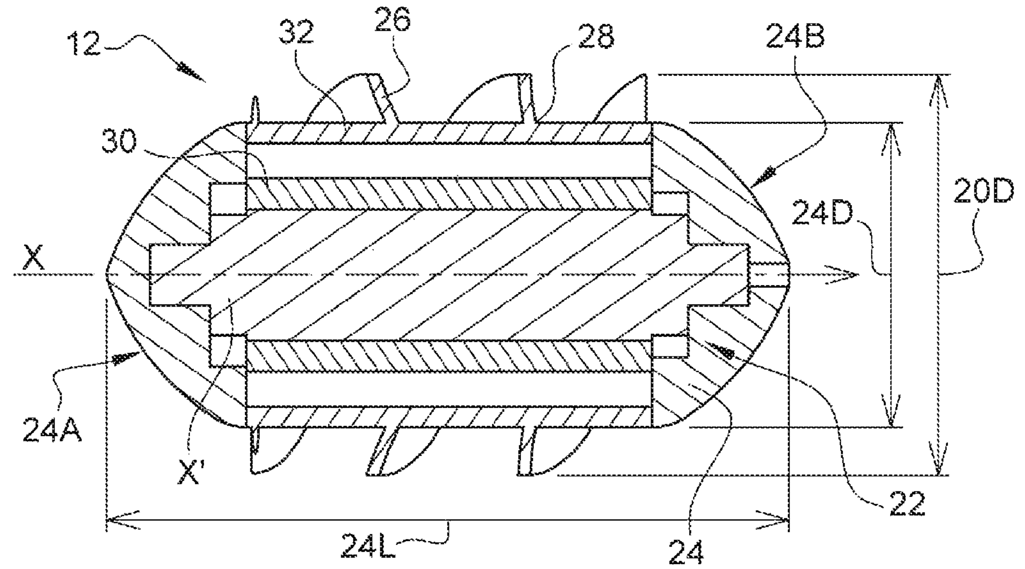
FIG. 4A is a schematic depiction of an axial cross section of the first embodiment of the impeller according to the invention.

In the embodiment shown on FIGS. 3A and 4A, the upstream extremity 24A and the downstream extremity 24B of the impeller hub 24 display each a tapered surface with an axially decreasing diameter. The impeller 20 therefore displays a general spindle shape. This spindle shape promotes favourable hydraulic performance of the device 10. Except at its extremities, the impeller hub 24 displays a diameter 24D comprised between 10 and 30 mm, preferably comprised between 15 and 25 mm.

Figure 3B:
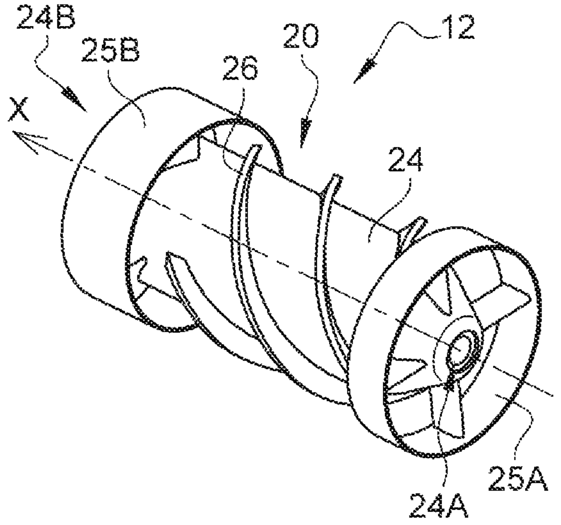
FIG. 3B is a perspective view of a second embodiment of the impeller according to the invention.
Figure 4B:
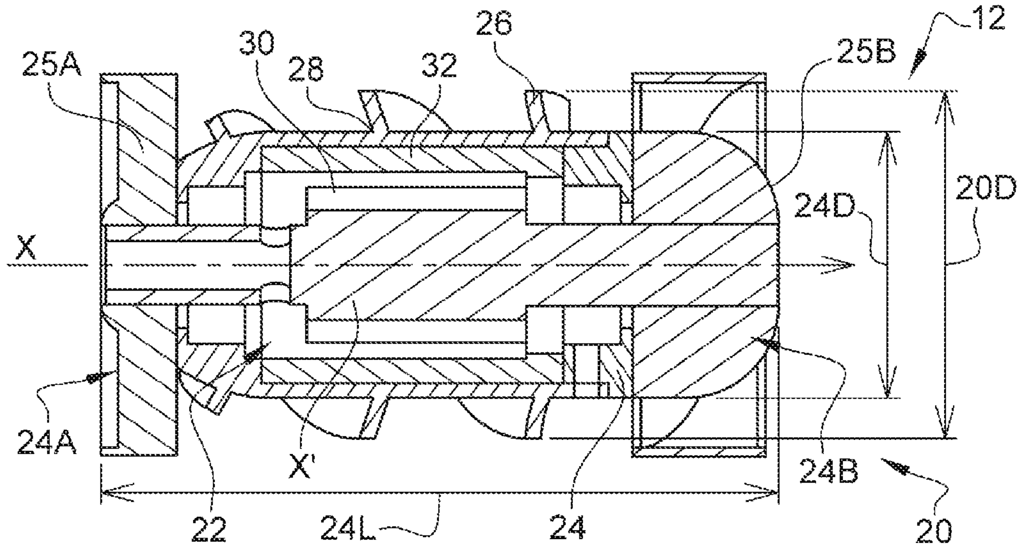
FIG. 4B is a schematic depiction of an axial cross section of the first second of the impeller according to the invention.

In the embodiment shown on FIGS. 3B and 4B, an inducer 25A added to upstream extremity 24A of the hub 24 and a diffuser 25B added to the downstream extremity 24B of the hub 24. These additions improve the flow pattern and generate more uniform flow. The inducer 25A and the diffuser 25B display a general cylindrical shape and might therefore provide two further fix elements connection structure 17 that can be used to anchor the hub 24 to the circular part 16. In this embodiment too, except at its extremities, the impeller hub 24 displays a diameter 24D comprised between 10 and 30 mm, preferably comprised between 15 and 25 mm.

Each impeller hub 24 of the embodiments illustrated on FIGS. 3A, 3B, 4A and 4B comprises four un-cupped blades 26. The blades 26 are configured to flow the blood towards the circular part 16 of the static anchoring element 14 and towards the discharge opening 16B.

In the embodiment illustrated on FIGS. 3A, 3B, 4A and 4B, each blade 26 displays an attachment area 28 running over the whole length of the impeller hub 24. The diameter 20D of the impeller 20 is comprised between 15 and 30 mm. In the embodiment shown in picture 3A and 4A, the impeller hub diameter 24D is 15 mm while the impeller diameter 20D is 20 mm. Regarding the size and shape of the impeller 20, a compromise has to be found between the impeller 20 efficiency and the wall shear stress ultimately leading to haemolysis.

The design of the impeller 20 leads the device 10 to generate a volume displacement of the blood flow. The aim of the device 10 is to come as close as possible to the natural mechanism of the left ventricle LV which, when normally working, sends 60-70 times per minute a given amount of blood into the ascending aorta A (the given volume depending on the person). This lead, regarding the natural blood circulation, to talk about volume displacement rather than a continuous flow with a given pressure which would correspond to an average pressure.

Minimizing the haemolysis and the thrombosis is a well-known constraint that needs to be taken into account. Haemolysis is the rupturing (lysis) of red blood cells contained within the blood and the release of their contents into the surrounding blood plasma. Haemolysis can lead to hemoglobinemia which can, among other dangerous consequences, lead to increased risk of infection due to its inhibitory effects on the innate immune system. Thrombosis is the formation of a blood clot inside a blood vessel or the left ventricle, obstructing the flow of blood through the circulatory system.

When the left ventricle LV unloading effect is achieved by an impeller 20, it is well known that both the blood flow rate and the haemolysis increase with the rotational speed of the impeller 20. Maintaining the flow rate constant while decreasing the rotational speed in order to limit the haemolysis can be achieved by increasing the diameter of the impeller 20. Maximizing the diameter 20D of the impeller 20 consequently enables to lower the required rotational speed to discharge the left ventricle LV.

In addition to the large circulation area 19 providing improved blood circulation, the device 10 according to the invention is particularly well adapted to good blood circulation since there is no sudden change of direction and since the impeller 20, with blood being driven towards the circular part 16 (the impeller 20 being of the centrifugal type), does not disturb significantly the blood flow as the diameter 20D of the impeller is relatively small compared to the diameter of the ferrule 16D. Therefore, the risks of haemolysis and thrombosis (clotting) are even further minimized.

The weight of the impeller 20 is comprised between 20 and 30 g. The impeller 20 of FIG. 3A weights sensibly 21 g. Regarding that the device 10 is implanted in a blood vessel portion P (for example the ascending aorta A), its weight has to be the lightest possible because a blood vessel is fragile and any damage risk for example a rupture of the wall 18) should be maintained as reduced as possible. Therefore, the lightest the device 10, the lower the risk of damaging the ascending aorta A. Further, as the circular part 16 aims at distributing the weight of the device 10 harmoniously over the wall 18, the traction forces said circular part 16 is subjected to (when the blood flow passes through) directly depend on the weight of the device 10 and are proportionally increasing with said weight.

In order to reduce the invasive character of the implantation, the blade 26 can be made of a foldable material. This way, the device 10 can be implanted inside the patient using an endovascular, transcatheter, minimally-invasive approach instead of being is implanted by performing a surgical incision and accessing to the ascending aorta A.

On FIG. 4A, it is to be seen that the impeller engine 22 is located inside the impeller hub 24. The engine is an electromagnetic engine comprising at least two coils 30 regularly distributed around the stator X' and at least one bearing magnet 32 secured to the rotor 12. The impeller engine 22 functions as any classical electromagnetic engine. However, the specific «outer rotor design» provides several performance advantages:

- to house the stator X', the rotor 12 of an "outer rotor motor" is by necessity larger than the rotor of a conventional "inner rotor motor", meaning that this kind of motor displays a higher inertia, which helps to dampen torque ripple (a common problem in conventional motors) and provides smooth, stable operation, even at low speeds,
- "outer rotor motors" typically produce higher torque than comparably sized "inner rotor designs". As well known in the art, torque is a product of the magnetic force times the radius of the air gap (length of magnetic flux). For a given motor diameter, "outer rotor motors" have a larger air gap area than "inner rotor motors", and the larger air gap allows a higher force to build, "outer rotor motors" have a larger area for flux to develop, and a larger air gap radius, which acts as the "lever arm" for torque production, «outer rotor motors» are axially shorter than inner rotor motors with similar performance characteristics.

Their compact size and high torque production make «outer rotor motors» a better choice for use in applications in need of high-precision, such as optical drives. Their smooth, consistent speed and steady output torque is a benefit over other motor types.

Preferably, the impeller engine 22 never stops rotating but rather lowers its speed so that the impeller 20 does no longer generate any flow (remaining at a possible residual speed around 1000 rpm).

The efficiency of the left ventricle LV unloading increases with the proportion of pumped blood flow driven by the device 10.

The coronary arteries CA (see FIG. 2B) are the only arteries which are perfused during the diastole. Once the ventricular contraction is finished, the pressure inside the ascending aorta A is briefly higher than the pressure inside the emptied left ventricle LV and this leads to a natural «inverse blood volume displacement» where blood is displaced towards the left ventricle LV and therefore enters the coronary arteries CA. Those coronary arteries cannot be perfused during the systole because they are immediately situated at the heart H exit.

The ascending aorta A thus defines the most favourable implantation site. However, due to the immediate proximity of the aortic valve AV which connects the left ventricle LV to the ascending aorta A (see FIG. 2B), the unloading action of the device 10 needs to be synchronized with the heart. This synchronization is essential as any offset would impair the unloading effect of the device. This would prevent the left ventricle LV from recovering and would therefore be contra-productive. Further, a lack of synchronization would inhibit the aortic valve closure which would then permanently remain open.

Further advantages brought by an implantation in the ascending aorta A are:

an easier access to the implantation site, resulting in a simpler surgical procedure for the implantation, an increased possibility of replacing the device 10 in case of technical failure, a possibility of removing the device 10 as soon as the recovery of the left ventricle LV of the patient is confirmed.

The activation of the rotor 12 is a pulsatile activation. Said activation is synchronized with the patient's systole. A pulsatile activation allows, among other advantages to lower the power consumption of the device 10.

The systole is the part of the cardiac cycle during which some chambers of the heart H contract after refilling with blood. Cardiac systole is the contraction of the heart H in response to an electrochemical stimulus to the heart's cells (the cardiomyocytes).

In one embodiment, the pulsatile activation of the impeller engine 22 comprises two phases: a mechanical phase and an electrical phase.

During the mechanical phase, the impeller 22 is rotated by the patient's natural blood flow. This mechanical phase generates an electric current, said electric current inducing the electrical phase of the activation. During said electrical phase, the impeller 22 is rotated by the impeller engine 22. The mechanical phase lasts about approximately ⅔ seconds and the electrical phase lasts approximately ⅓ seconds.

In another embodiment, the pulsatile activation of the propeller is induced by signals sensed by sensors. For example, the cardiac electrical activity can be detected by electrical sensors either located subcutaneously or implanted inside the right ventricle or located near the impeller 20, and the sensed signals are used to synchronize the impeller engine 22 with the heart H systole. This embodiment allows the device 10 to anticipate and facilitate the opening of the aortic valve AV by anticipating the systole: triggered by the sensors, the device 10 might be activated just a bit before the systole in order to create a local depression in blood vessel portion P while the left ventricular pressure increases.

In both cases, the systole induces an increase in the rotational speed of the impeller 20.

This synchronization with the cardiac rhythm leads to the following advantages:

pulsatility and, as a benefit, reduction of the adverse events (an unfavourable and unintended sign, symptom, or disease temporally associated with the use of the device 10) reported on patients implanted with continuous-flow left ventricular assist device due, in particular, to a suboptimal vascularization of distalities, reduction of power consumption, accompanying the natural rhythm of the patient's blood flow.

It is known that the blood being discharged from the left ventricle LV during the heart systole displays a rotational forward movement. This rotational movement changes with every heart, meaning that some natural blood flows have a faster rotational movement that others and that the rotation direction is also heart dependent. Therefore, adapting the device 10 to the natural blood flow of each patient minimizes the disruption of the blood flow caused by the implantation of a mechanical device in a blood vessel.

In case the natural biological wall 18 of the blood vessel portion P is conserved, the rotor 12, the stator X' and the connection structure 17 can be removed from the patient by disconnecting the connection structure 17 from the circular part 16, which remains in place. Alternatively, the rotor 12 and the stator X' can be removed from the patient by disconnecting the stator X' from the connection structure 17, which remains in place within the circular part 16. In case the implanted device 10 replaces the natural biological wall 18 of the blood vessel portion P, the device 10 can nevertheless be removed from the patient: the missing natural biological wall 18 of the blood vessel portion P will be replaced with a well-known vascular prosthesis.

Figure 5A:
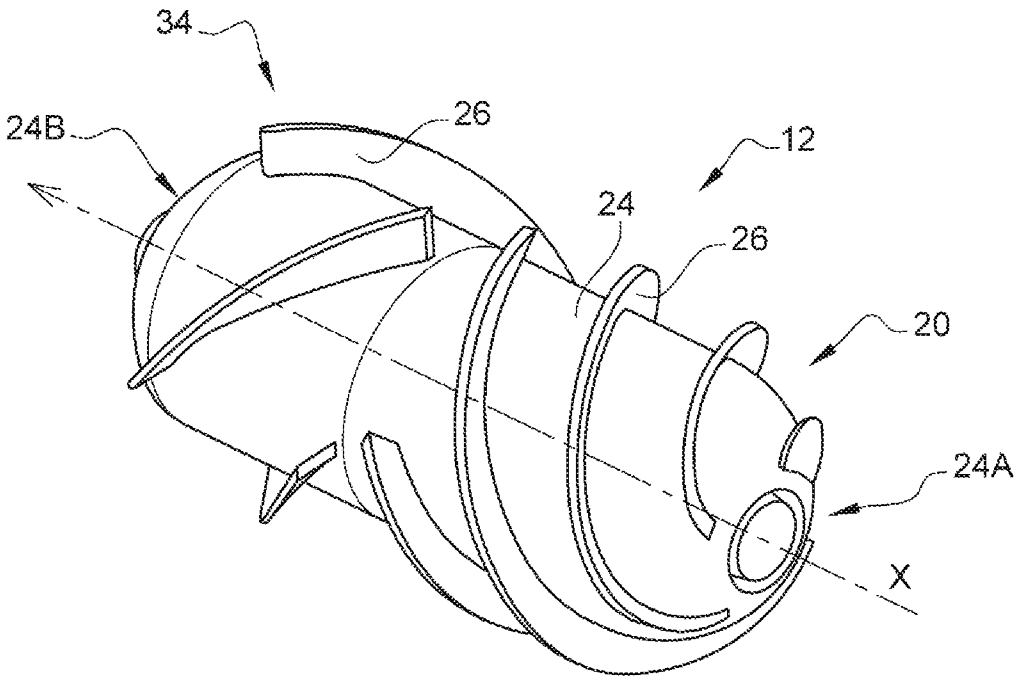
FIG. 5A is a perspective view of a third embodiment of the impeller according to the invention.
Figure 5B:
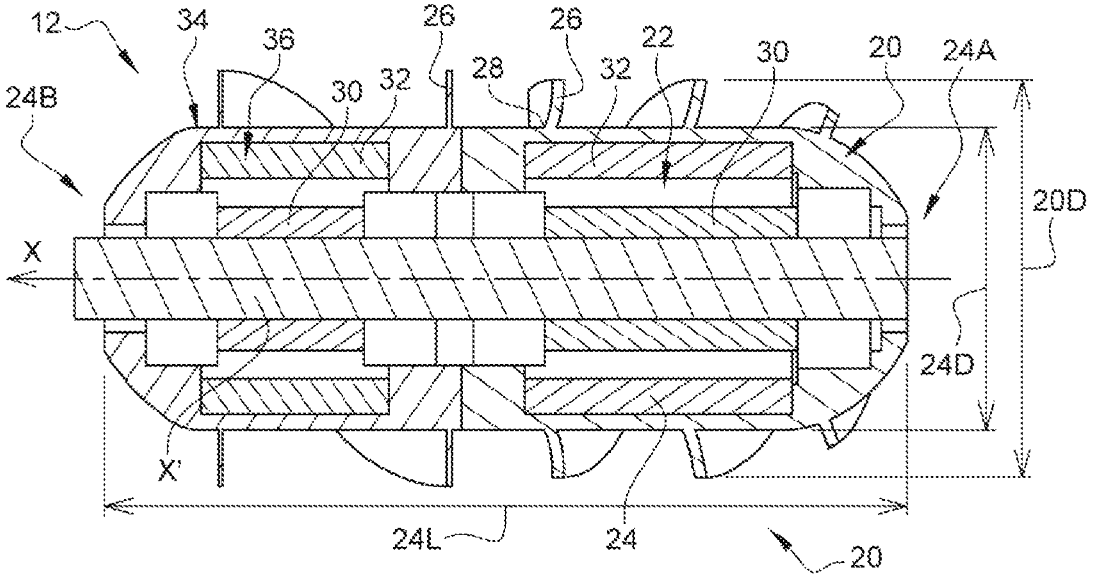
FIG. 5B is a schematic depiction of an axial cross section of the third embodiment of the impeller according to the invention.

In a third embodiment illustrated on FIGS. 5A and 5B, comprises a second impeller 34 in addition to the impeller 20, thus forming a contra-rotative impeller device 10. In this embodiment, both impellers 20, 34 extend along the same stator X'. More precisely, the second impeller 34 follows, downstream, the impeller 20 along the axial direction X. The benefit of using two impellers rotating into opposite direction is to provide better hemodynamic performance. As can be seen on FIG. 5B, the second impeller 34 is driven by a second impeller engine 36. This second impeller engine 36 displays a similar design and works in a similar way than the impeller engine 22. However, the rotation direction of the second impeller 36 is opposite to the rotation direction of the impeller 20.

In a further embodiment, not shown, the second impeller 34 is also driven by the impeller engine 22. Both impellers 20, 34 are therefore driven by the impeller engine 22. The second impeller 34 is connected to the impeller engine 22 by means of an epicyclic gear train. This allows the second impeller 34 to rotate in a direction being the opposite of the rotation direction of the impeller 20.

The benefit of a contra-rotating impeller is the absence of rotational blood flow, this allowing the pushing of a maximum amount of blood, uniformly through the device 10. This results in high performance and low induced energy loss. It also allows to counter the asymmetrical torque effect generated of a single impeller.

In the embodiment illustrated on FIGS. 5A and 5B, each blade 26 displays an attachment area 28 running over half of the length of the impeller hub 24. It might also, for example, be a ⅓-⅔ hub length ratio. The diameter 20D of both impellers 20, 34 are the same and are comprised between 15 and 30 mm.

However, the impeller engine(s) 22, 36 and impeller(s) 20, 34 of the device 10 should be able to operate both continuous mode (independently of the systolic rhythm of the heart H) and pulsatile mode (induced by the systolic rhythm of the heart H). The continuous mode is configured to be used for testing purposes Regarding all the here-above detailed technical features, the present invention enables a more favourable benefits/risk ratio regarding a patient's health and therefore allowing, firstly, the treatment of patients at an earlier stage of the disease, and secondly a rehabilitation of the patient's heart. The current invention therefore allows to maximizing the unloading efficiency while preserving the blood circulation, perfusing the supra-aortic trunks and preserving the cardiac architecture. This allows to address patients at an earlier stage of the disease.

While various embodiments have been described and illustrated, the detailed description is not to be construed as being limited hereto. Various modifications can be made to the embodiments by those skilled in the art without departing from the true spirit and scope of the disclosure as defined by the claims.

The invention claimed is:

1. A ventricle unloading device intended to be serially implanted inside a patient's blood vessel portion through which a blood flow circulates, said device comprising:

a stator, a rotor arranged around the stator, the rotor comprising a blood driving impeller and at least a part of an impeller engine, the impeller comprising a hub and at least one blade displaying an attachment area to the hub, the impeller further being an unducted impeller aimed at rotating freely within the blood vessel portion, and a static anchoring element displaying a circular part which is configured to extend around the impeller, wherein the circular part of the static anchoring element defines a circulation area intended to contain the entire blood flow circulating through the blood vessel portion, wherein the activation of the rotor is a pulsatile activation and that said activation is synchronized with the patient's heart contraction.

2. The device according to claim 1, wherein the circular part of the static anchoring element is configured to extend against a wall of the blood vessel portion and to cooperate by friction with said wall.

3. The device according to claim 1, wherein the circular part of the static anchoring element is configured to form at least a part of a wall of the blood vessel portion.

4. The device according to claim 3, wherein the circular part of the static anchoring element comprises a rigid body and two soft and flexible extremities, in order to enable anastomosis.

5. The device according to claim 4, wherein the device is located in the patient's ascending aorta.

6. The device according to claim 4, wherein the impeller is made of a foldable material.

7. The device according to claim 4, wherein the impeller engine is located inside the impeller hub.

8. The device according to claim 4, wherein the impeller displays a length comprised between 20 and 50 mm.

9. The device according to claim 4, wherein the pulsatile activation of the impeller engine comprises two phases:

a mechanical phase during which the impeller is rotated by the patient's natural blood flow, and an electrical phase during which the impeller is rotated by the impeller engine.

10. The according to claim 9, wherein the mechanical phase of the activation generates an electric current, said electric current inducing the electrical phase of the activation.

11. The device according to claim 4, wherein the pulsatile activation of the impeller is induced by signals sensed by electrical sensors.

12. The device according to claim 4, wherein the rotation direction of the impeller depends on the natural direction of the patient's blood flow rotation.

13. The device according to claim 4, wherein the device comprises a second impeller, said second impeller extending along the stator and being driven by a second impeller engine, the rotation direction of the second impeller being opposite to the rotation direction of the impeller.

14. The device according to claim 4, wherein the device comprises a second impeller, said second impeller extending along the stator, both impeller being driven by the impeller engine, the second impeller being connected to the impeller engine by means of an epicyclic gear train in order to allow the second impeller rotation direction to be opposite to the rotation direction of the impeller.

* * * * *